(12) United States Patent
Umeda et al.

(10) Patent No.: US 7,652,155 B2
(45) Date of Patent: Jan. 26, 2010

(54) DIAMINE DERIVATIVE, PRODUCTION PROCESS THEREFOR AND ANTIOXIDANT

(75) Inventors: Nobuhiro Umeda, Odawara (JP); Nobuo Mochizuki, Odawara (JP); Seiichi Uchida, Odawara (JP); Seiichi Ikeyama, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 533 days.

(21) Appl. No.: 10/552,015

(22) PCT Filed: Apr. 13, 2004

(86) PCT No.: PCT/JP2004/005240

§ 371 (c)(1),
(2), (4) Date: Oct. 11, 2005

(87) PCT Pub. No.: WO2004/092153

PCT Pub. Date: Oct. 28, 2004

(65) Prior Publication Data

US 2006/0194872 A1 Aug. 31, 2006

(30) Foreign Application Priority Data

Apr. 14, 2003 (JP) .............................. 2003-109665
Jan. 30, 2004 (JP) .............................. 2004-022719

(51) Int. Cl.
*C07D 311/00* (2006.01)
*C07D 307/00* (2006.01)
(52) U.S. Cl. ...................... 549/408; 549/429; 549/469
(58) Field of Classification Search ................ 514/456;
549/408, 429, 469
See application file for complete search history.

(56) References Cited

FOREIGN PATENT DOCUMENTS

| | | |
|---|---|---|
| CA | 2382418 A1 | 3/2001 |
| DE | 3407505 A1 | 9/1985 |
| EP | 0 324 377 A2 | 7/1989 |
| EP | 0 345 593 A1 | 12/1989 |
| EP | 0377450 A1 | 7/1990 |
| EP | 0 458 037 A1 | 11/1991 |
| EP | 0 483 772 A1 | 5/1992 |
| EP | 0483772 A1 | 5/1992 |
| JP | 55-069567 A | 5/1980 |
| JP | 61-044840 A | 3/1986 |
| JP | 01-104033 A | 4/1989 |
| JP | 02-076869 A | 3/1990 |
| JP | 02-121975 A | 5/1990 |
| JP | 2-288856 | 11/1990 |
| JP | 5-140142 | 6/1993 |
| JP | 05-140142 A1 | 6/1993 |
| JP | 5-310724 | 11/1993 |
| JP | 06-228136 A | 8/1994 |
| JP | 06-287139 A | 10/1994 |
| JP | 8-503922 | 4/1996 |
| WO | WO-93/20057 | 10/1993 |
| WO | WO-95/29163 A1 | 11/1995 |
| WO | WO-96/28437 A1 | 9/1996 |
| WO | WO-00/06550 A1 | 2/2000 |
| WO | WO-00/07581 A2 | 2/2000 |
| WO | WO-01/14834 A1 | 3/2001 |
| WO | WO-01/68610 A1 | 9/2001 |
| WO | WO-03/022821 A1 | 3/2003 |

OTHER PUBLICATIONS

Patent Abstracts of Japan for JP61-044840 published Mar. 4, 1986.
Patent Abstracts of Japan for JP01-104033 published Apr. 21, 1989.
Patent Abstracts of Japan for JP02-121975 published May 9, 1990.
Patent Abstracts of Japan for JP55-069567 published May 26, 1980.
Patent Abstracts of Japan for JP05-140142 published Jun. 8, 1993.
Patent Abstracts of Japan for JP06-228136 published Aug. 16, 1994.
Patent Abstracts of Japan for JP02-076869 published Mar. 16, 1990.
Patent Abstracts of Japan for JP06-287139 published Oct. 11, 1994.
Truscott R.J.W., et al., "The state of sulphydryl groups in normal and cataractous human lenses.", Exp. Eye Res., 1977, vol. 25, pp. 139-148.
Scott John W., et al., "6-Hydroxychroman-2-carbioxylic Acids: Novel Antioxidants1" Journal of the American Oil Chemists' Society, vol. 51, pp. 200-203, 1974.
Cyrus Tillman, et al., "Disruption of the 12/15-lipoxygenase gene diminishes atherosclerosis in apo E-deficient mice". The Journal of Clinical Investigation. Jun. 1999, vol. 103, No. 11, pp. 1597-1604.
Anderson RE, et al. "Free radicals and ocular disease", Adv. Exp. Med. Biol. 1994; 366: pp. 73-86.
Nishigori H. et al., "The alteration of lipid peroxide in glucocorticoid-induced cataract of developing chick embryos and the effect of the ascorbic acid.", Curr Eye Res. Jan. 1986;5(1); 37-40.
Hiramitsu T, et al. "Preventive effect of anitoxidants on lipid peroxidation in the retina.", Ophthalmic Res. 1991;23(4);196-203.
Vitamin Information Center (Tokyo), VIC Newsletter, 105, 4, 2002.
J. Act. Free Rad., vol. 3, No. 4, 1992, pp. 444-449.

(Continued)

*Primary Examiner*—Taylor Victor Oh
(74) *Attorney, Agent, or Firm*—Darby & Darby PC

(57) ABSTRACT

The present invention relates to a compound represented by formula (1):

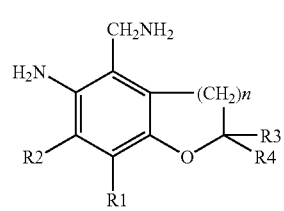

(1)

(wherein, R1, R2, R3 and R4 respectively and independently represent a hydrogen atom or a $C_{1-6}$ alkyl group, and n represents an integer of 1 or 2) and a production process thereof, as well as an antioxidant that contains the compound as its active ingredient, and a kidney disease treatment agent, cerebrovascular disorder treatment agent, retina oxidative disorder inhibitor and lipoxygenase inhibitor that contain the antioxidant.

3 Claims, No Drawings

OTHER PUBLICATIONS

Solbach U, et al., "Imaging of retinal autofluorescence in patients with age-related macular degeneration.", Retina., 1997; 17(5): 385-389.

Patent Abstracts of Japan for 2004-010513 published Jan. 15, 2004.

Harder DR, "Role of cytochrome P-450 enzymes and metabolites of arachidonic acid in the control of vascular tone.", J Vasc Res. Mar.-Apr. 1995; 32(2):79-92.

McGiff John C., et al., "20-HETE and the kidney: resolution of old problems and new beginnings.", Invited Review, the American Physiological Society, 1999, pp. R607-R623.

Roman Richard J., $P$-450 Metabolites of Archidonic Acid in the Control of Cardiovascular Function, Physiol Rev, vol. 82, Jan. 2002, pp. 131-186.

C.D. Funk, "Lipids and Lipid Metabolism", Biochimica et Biophysica Acta 1304, 1996, pp. 65-84.

Anderson Robert E. et al., "Free Radicals and Ocular Disease",pp. 73-86, 1994.

Nishigori Hideo, et al., "The Alteration of Lipid Peroxide in Glucocorticoid-induced Cataract of Developing Chick Embryos and the Effect of Absorbic Acid.", Current Eye Res., vol. 5, No. 1, 1986, pp. 37-40.

Truscott R.J.W., et al., "The state of sulphydryl groups in normal and cataractous human lenses.", Exp. Eye Res., 1997, vol. 25, 139-148.

Hiramitsu Tadahisa, et al., "Preventive effect of antioxidants on lipid peroxidation in the retina.", Ophthalmic Res, 1991; vol. 23; pp. 196-203.

Solbach Uta MD, et al., "Imaging of retinal autofluorescence in patients with age-related macular degeneration.", Retina, Journal of Retinal and Vitreous diseases, 1997, vol. 17, No. 5, pp. 385-389.

Ohkawa S., et al., "5-Aminocoumarans: Dual Inhibitors of Lipid Peroxidation and Dopamine Release with Protective Effects Against Central Nervous Sstem Trauma and lschemia.", Journal of Med. Chem. 1997, vol. 40, pp. 559-573.

DIAMINE DERIVATIVE, PRODUCTION PROCESS THEREFOR AND ANTIOXIDANT

CROSS-REFERENCE TO PRIOR APPLICATION

This is a U.S. National Phase application under 35 U.S.C. §371 of International Patent Application No. PCT/JP2004/005240 filed Apr. 13, 2004, and claims the benefit of Japanese Patent Application Nos. 2003-109665 filed Apr. 14, 2003 and 2004-022719 filed Jan. 30, 2004, all of which are incorporated by reference herein. The International Application was published in Japanese on Oct. 28, 2004 as WO 2004/092 153 A1 under PCT Article 21(2).

TECHNICAL FIELD

The present invention relates to a novel diamine derivative, a production process therefor, an antioxidant having the compound as its active ingredient, and a kidney disease treatment agent, cerebrovascular disease treatment agent, retinal oxidation disorder inhibitor and lipoxygenase inhibitor that uses the antioxidant.

BACKGROUND ART

The formation of lipid peroxides in the body and their associated radical reactions have recently been demonstrated to have various detrimental effects on the body resulting from membrane damage, cytotoxicity and so forth. Accompanying this finding, various attempts have been made to apply antioxidants and lipid peroxide formation inhibitors to pharmaceuticals, and research has been conducted on numerous types of antioxidants (see, for example, Non-Patent Literature 1). Known examples of these antioxidants include pharmaceutical compositions used for the treatment and prevention of endotoxin shock triggered by inflammation or infection that contain a specific quinone derivative (see, for example, Patent Literature 1), hydroxamic acid derivatives used for the treatment and prevention of autoimmune diseases having cell growth inhibitory action and vascularization inhibitory action (see, for example, Patent Literature 2), and 2,3-dihydrobenzofuran derivatives that are useful as antioxidants and radical scavengers (see, for example, Patent Literatures 3, 4 and 5). In addition, other known examples include imidazole-based compounds having anti-hyperlipemia action that are useful for the treatment and prevention of arteriosclerosis (see, for example, Patent Literature 6), and benzothiazine carboxamides represented by the following formula having anti-arthritis activity (see, for example, Patent Literature 7).

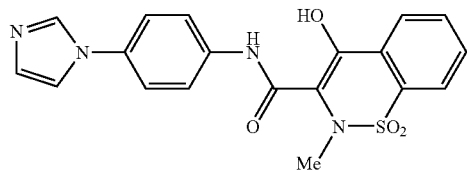

Moreover, other known examples include carbonyl aminophenyl imidazole derivatives (see, for example, Patent Literature 8, Patent Literature 9, and Patent Literature 10), aminodihydrobenzofuran derivatives having lipid peroxide formation inhibitory action that are useful as preventive and treatment agents of various diseases such as arteriosclerosis, liver disease and cerebrovascular disorders (see, for example, Patent Literature 11), anti-hyperlipemia drugs containing phenylazole compounds (see, for example, Patent Literature 12), dihydrobenzofuran derivatives that significantly improve damage caused by lipids, proteins, carbohydrates and DNA occurring as a result of oxidative stress that occurs when antioxidation defense systems are inadequate (see, for example, Patent Literature 13), and optically active aminodihydrobenzofuran derivatives that are effective for improving, treating and preventing impairment of brain function accompanying cerebral stroke or head injury.

Since the brain is dependent on circulating blood for its supply of energy despite it having a large energy demand, it is extremely susceptible to ischemia. When the brain falls into a state of cerebral ischemia as a result of having its blood flow cut off for various reasons, active oxygen species are formed triggered by mitochondrial damage and elevated calcium levels within nerve cells. In addition, oxygen radicals are known to be formed in extremely large amounts when blood flow is resumed following ischemia. These active oxygen species ultimately act on lipids, proteins, nucleic acids, or the like, which is said to result in their oxidation and cell death. Antioxidants are used to treat such a condition, and in Japan, Edaravone has been approved as a brain protective drug and is used for that purpose.

Lipoxygenase (abbreviated as LO), which adds oxygen to unsaturated fatty acids such as arachidonic acid, is known to exist in the form of 5-LO, 8-LO, 12-LO and 15-LO according to the site where oxygen is added. Among these, 5-LO is the initial enzyme in the synthesis of leucotrienes, which are potent inflammation mediators. Leucotrienes are involved in various inflammatory diseases such as asthma, rheumatoid arthritis, inflammatory colitis and psoriasis, and their control is useful for the treatment of these diseases. 12-LO and 15-LO react with linoleic acid, cholesterol esters, phospholipids and low-density lipoproteins (hereinafter, abbreviated as LDL) in addition to arachidonic acid, and are known to add oxygen to their unsaturated fatty acids (see Non-Patent Literature 2). Macrophages become foamy cells by unrestricted uptake of oxidative-modified LDL by means of scavenger receptors, and this is widely known to be the initial step in the formation of arteriosclerotic foci. 12-LO and 15-LO are expressed in high levels in macrophages, and have been clearly demonstrated to be essential as the trigger for oxidative modification of LDL (see Non-Patent Literature 3). Their control is useful for the treatment of various types of diseases caused by arteriosclerosis (see Patent Literature 15).

Oxidative stress involving free radicals and active oxygen is thought to be one of the causative factors of many eye diseases such as cataract and macular degeneration that frequently occurs with aging (see, for example, Non-Patent Literatures 4, and 6). Among tissues of the eye, the retina along with the lens are known to be tissues that are susceptible to the effects of aging (see, for example, Non-Patent Literature 7). The retina is susceptible to the effects of various free radicals because it contains a large amount of higher unsaturated fatty acids and because it is provided with nutrients from both retinal blood vessels and choroid blood vessels and consumes a large amount of oxygen. For example, light such as sunlight that enters the eyes during the entire course of a person's life is a typical example of oxidative stress that affects the retina. The majority of the sunlight that reaches the earth consists of visible light and infrared right, while ultraviolet light that only accounts for several percent of that light has a significant effect on health by powerfully interacting with the body as compared with visible light and infrared light. Ultraviolet light is divided into UV-A (320 to 400 nm), UV-B (280 to 320 nm) and V-C (190 to 280 nm) according to differences in its wavelength, and although its action and strength relative to the body differ, ultraviolet light of 290 nm or less which exhibits particularly strong cytotoxicity has conventionally been thought to hardly reach the earth's surface at all as a result of being absorbed by the ozone layer of the stratosphere. In recent years however, the amount of ultraviolet light that reaches the earth has increased due to the appearance of ozone holes thought to be caused by destruction of the environment, and judging from rapid increases in the occurrences of skin disorders and skin cancer related to ultraviolet light in the southern hemisphere, retinopathy is expected to considerably increase due to the effects of UV-A reaching the earth's surface.

Among various eye diseases, age-related macular degeneration is a type of retinopathy associated with a high degree of vision loss. In the US, roughly 10 million people have mild symptoms of this disease, and more than 450,000 have impaired vision brought on by this disorder (see, for example, Non-Patent Literature 8). There is concern over an increased incidence of this disease in Japan as well where the number of elderly in the general population is increasing rapidly. Although there are many aspects of the mechanism of occurrence of macular degeneration that are not fully understood, the progression of this lesion has been pointed out to involve a peroxidation reaction caused by light absorption in the retina (see, for example, Non-Patent Literatures 9 and 10). In addition, the appearance of a lipofuscini-like fluorescent substance known as Druse has been observed in the early stages of its onset. Since lipofuscin is formed from the bonding of protein and aldehyde, which is a secondary decomposition product of lipid peroxides, there is the possibility that a lipid peroxidation reaction in the retina caused by ultraviolet light or visible light may induce this type of retinopathy.

Retina disease treatment agents containing a specific dihydrofuran derivative (see, for example, Patent Literature 16), and drugs for visual acuity and retinal changes, including macular changes of the retina, that contain propionyl L-carnitine or its pharmaceutically acceptable salts, and carotenoids (see, for example, Patent Literature 17), are known to be useful for the prevention and treatment of these retina diseases due to their antioxidative action.

Patent Literature 1: Japanese Unexamined Patent Application, First Publication No. S61-44840

Patent Literature 2: Japanese Unexamined Patent Application, First Publication No. H1-104033

Patent Literature 3: Japanese Unexamined Patent Application, First Publication No. H2-121975

Patent Literature 4: European Patent Application, Publication No. EP 345593

Patent Literature 5: European Patent Application, Publication No. EP 483772

Patent Literature 6: International Publication No. WO 95/29163

Patent Literature 7: German Patent Application, Publication No. DE 3,407,505

Patent Literature 8: Japanese Unexamined Patent Application, First Publication No. S55-69567

Patent Literature 9: European Patent Application No. EP 324277

Patent Literature 10: European Patent Application, Publication No. EP 458037

Patent Literature 11: Japanese Unexamined Patent Application, First Publication No. H5-140142

Patent Literature 12: International Publication No. WO 00/006550

Patent Literature 13: International Publication No. WO 96/28437

Patent Literature 14: Japanese Unexamined Patent Application, First Publication No. H6-228136

Patent Literature 15: Japanese Unexamined Patent Application, First Publication No. H2-76869

Patent Literature 16: Japanese Unexamined Patent Application, First Publication No. H6-287139

Patent Literature 17: International Publication No. WO 00/07581

Non-Patent Literature 1: J. Amer. Oil Chemists Soc., 51, 200, 1974.

Non-Patent Literature 2: Biochem. Biophys. Acta, 1304, 65, 1996.

Non-Patent Literature 3: J. Clin. Invest., 103, 1597, 1999.

Non-Patent Literature 4: Anderson R. E., Kretzer F. L., Rapp L. M.: "Free Radicals and Eye Diseases", Adv. Exp. Med. Biol., 366, 73, 1994.

Non-Patent Literature S: Nishigori H., Lee J. W., Yamauchi Y., Iwatsuru M.: "Lipid Peroxide Changes in Glucorticoid-Induced Cataract in Germinated Chicken Embryos and Effects of Ascorbic Acid", Curr. Eye Res., 5, 37, 1986.

Non-Patent Literature 6: Truscott R. J. W., Augusteyn R. C.: "Action of Mercapto Groups in the Normal and Cataract Human Lens", Exp. Eye Res., 25, 139, 1977.

Non-Patent Literature 7: Hiramitsu T., Armstrong D.: "Preventive Effects of Antioxidants Against Lipid Peroxidation Reactions in the Retina", Ophthalmic Research, 23, 196, 1991.

Non-Patent Literature 8: Vitamin Information Center (Tokyo), VIC Newsletter, 105, 4, 2002.

Non-Patent Literature 9: Komura S.: "Cataract and Active Oxygen Free Radicals", 3, 444, 1992.

Non-Patent Literature 10: Solbach U., Keilhauer C., Knabben H., Wolf S.: "Retina Autofluorescent Images in Age-Related Macular Degeneration", Retina, 17, 385, 1997.

DISCLOSURE OF THE INVENTION

The object of the present invention is to provide an antioxidant that is effective for the treatment of arteriosclerosis and other ischemic organ disorders such as myocardial infarction and cerebral stroke or for the treatment of diseases caused by oxidative cytotoxicity, and to provide an oxidation disorder inhibitor for the retina that inhibits retinopathy caused by oxidation, and particularly photooxidation, and a lipoxygenase inhibitor.

As a result of conducting extensive studies to solve the aforementioned problems, the inventors of the present invention determined that the cause of the inadequate effectiveness of existing antioxidants is that the drug either does not reach the target site or ends up losing activity before reaching the target site, and as a result of conducting extensive studies for the purpose of developing an antioxidant that has better organ migration and passes easily through the blood-brain barrier or blood-retina barrier in particular, found that a compound represented by formula (1) achieves the desired effect, and that it has superior in vivo antioxidative action regardless of the administration route, thereby leading to completion of the present invention.

Moreover, the inventors of the present invention also studied effects on the retina by subjecting rat eyes to spot irradiation with a fixed dosage of UV-A. A lipofuscin-like fluorescent substance is frequently detected from the reaction product of proteins and aldehydes originating in lipid peroxides during the early stages of onset of retina diseases having a high degree of vision loss such as macular degeneration. An increase in protein in the vicinity of 66 kDa is observed that is highly proportional to changes in eye retina tissue irradiated with UV-A, and this protein has been observed to be an albumin-like substance based on the results of instrument analyses and studies using albumin-free rats. Since significant increases in a lipofuscin-like fluorescent substance have been observed due to the presence of albumin in automated oxidation reactions of retina tissue in vitro, there is a high probability that abnormal increases in some proteins in retina tissue caused by UV-A irradiation are related to increases in fluorescent substances in the retina, and that this triggers retinopathy. The inventors of the present invention have previously conducted studies on retinopathy inhibitors by using changes in this retina protein as the first biochemical indicator. During the course of those studies, the compound according to the present invention having strong antioxidative action was observed to migrate to the retina in a short period of time following oral administration, and significantly inhibited increases in the 66 kDa protein caused by UV-A spot irradiation. After obtaining findings that the compound according to the present invention is effective against retinopathy caused by oxidation, and particularly effective in diminishing the progress and symptoms of age-related macular degeneration of the retina that increases with age, this result led to completion of the present invention on the basis of those findings.

Namely, the present invention is characterized by the following.

1. A compound represented by formula (1):

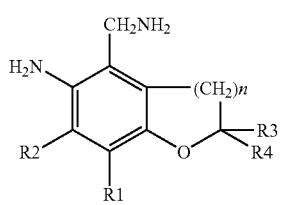

(1)

(wherein, R1, R2, R3 and R4 respectively and independently represent a hydrogen atom or a $C_{1-6}$ alkyl group, and n represents an integer of 1 or 2).

2. A production process of a compound represented by formula (1):

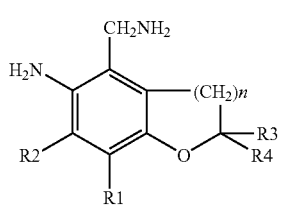

(1)

(wherein, R1, R2, R3, R4 and n are the same as previously defined) comprising:

a step 1 in which a compound represented by formula (3):

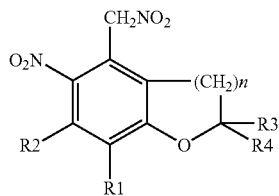

(3)

(wherein, R1, R2, R3, R4 and n are the same as previously defined) is obtained by nitrating a compound represented by formula (2):

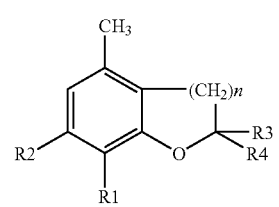

(2)

(wherein, R1, R2, R3, R4 and n are the same as previously defined); and, a step 2 in which the resulting compound is converted to an amino group using a reducing agent.

3. An antioxidant that contains as its active ingredient at least one compound represented by formula (1):

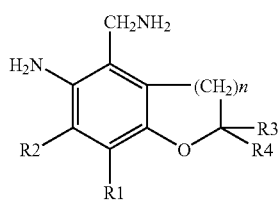

(1)

(wherein, R1, R2, R3, R4 and n are the same as previously defined) or a pharmaceutically acceptable salt thereof.

4. A kidney disease, cerebrovascular or circulatory disease treatment agent containing the antioxidant as described in 3.

5. A cerebral infarction treatment agent containing the antioxidant as described in 3.

6. A retinal oxidation disorder inhibitor containing the antioxidant as described in 3.

7. A retinal oxidation disorder inhibitor as described in 6 for age-related macular degeneration or diabetic retinopathy.

8. A lipoxygenase inhibitor containing the antioxidant as described in 3.

BEST MODE FOR CARRYING OUT THE INVENTION

R1, R2, R3 and R4 in the definition of the aforementioned formula (1) respectively and independently represent a hydrogen atom or a $C_{1-6}$ alkyl group such as methyl, ethyl, n-propyl, isopropyl, n-butyl, sec-butyl, isobutyl or t-butyl.

(Compound Production Process)

A compound of the present invention represented by the aforementioned formula (1) can be produced, for example, in the manner described below. However, a compound of the present invention can also be synthesized by a generally known method, and there are no limitations to that method.

Production Step 1:

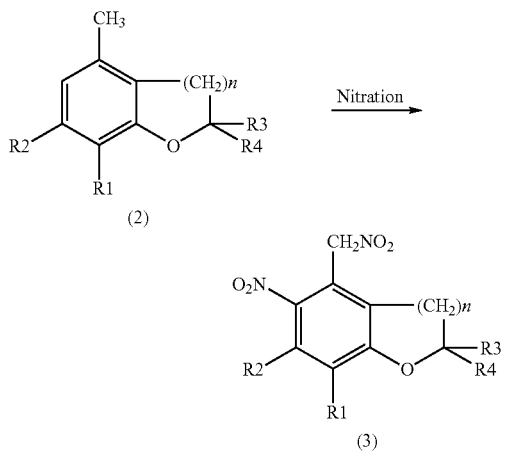

(In the formulas, R1, R2, R3, R4 and n are the same as previously defined).

Namely, a compound represented by formula (3) is obtained by nitrating a compound represented by formula (2). This nitration reaction consists of nitration using nitric acid or fuming nitric acid in acetic acid or acetic acid anhydride. The reaction is carried out at −30° C. to roughly the boiling point of the solvent, and is preferably carried out at −10° C. to 30° C.

Production Step 2:

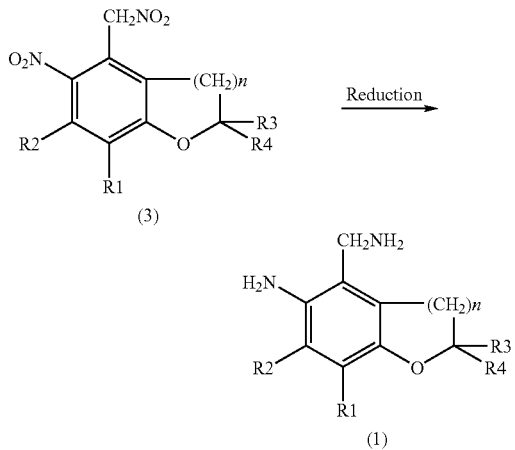

(In the formulas, R1, R2, R3, R4 and n are the same as previously defined).

Namely, a compound represented by formula (1) is obtained by carrying out hydrogenation using a catalyst on a compound represented by formula (3). Examples of catalysts include palladium carbon, platinum dioxide, Raney nickel, and the like. Examples of solvents that can be used include alcohols such as methanol and ethanol, ethers such as diethyl ether, THF and 1,4-dioxane, hydrocarbons such as benzene, toluene, xylene and cyclohexane, amides such as DMF, organic acids such as formic acid and acetic acid, esters such as ethyl acetate and mixed solvents thereof. The reaction is carried out at 0° C. to roughly the boiling point of the solvent, and is preferably carried out at 20° C. to 80° C.

The structure of the compound of the present invention is determined by IR, NMR and MS.

Furthermore, the compound represented by the aforementioned formula (1) and the raw material compounds represented by the aforementioned formulas (2) and (3) can also have several optically active forms. These are all included in the scope of the present invention.

Examples of pharmaceutically acceptable salts of the compound represented by the aforementioned formula (1) include salts of inorganic acids such as hydrochloric acid, sulfuric acid, nitric acid and phosphoric acid, and salts of organic acids such as acetic acid, propionic acid, lactic acid, succinic acid, tartaric acid, citric acid, benzoic aced, salicylic acid nicotinic acid and heptagluconic acid. These can be easily produced by ordinary chemical synthesis methods.

Although typical examples of the compound of the present invention (formula (1)) that can be produced in the manner described above are shown in Table 1, the compound according to the present invention is not limited thereto. In addition, their pharmaceutically acceptable salts such as hydrochlorides are also included in the typical examples. Furthermore, an abbreviation in the table has the following meaning.

Me: Methyl

TABLE 1

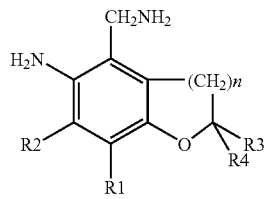

| R1 | R2 | R3 | R4 | n |
|----|----|----|----|---|
| H  | H  | H  | H  | 1 |
| H  | H  | H  | Me | 1 |
| H  | H  | Me | H  | 1 |
| H  | H  | Me | Me | 1 |
| H  | Me | H  | H  | 1 |
| H  | Me | H  | Me | 1 |
| H  | Me | Me | H  | 1 |
| H  | Me | Me | Me | 1 |
| Me | H  | H  | Me | 1 |
| Me | H  | H  | Me | 1 |
| Me | H  | Me | H  | 1 |
| Me | H  | Me | Me | 1 |
| Me | Me | H  | H  | 1 |
| Me | Me | Me | H  | 1 |
| Me | Me | Me | Me | 1 |
| Me | Me | Me | Me | 1 |
| H  | H  | H  | H  | 2 |
| H  | H  | H  | Me | 2 |
| H  | H  | Me | H  | 2 |
| H  | H  | Me | Me | 2 |
| H  | Me | H  | H  | 2 |
| H  | Me | H  | Me | 2 |
| H  | Me | Me | H  | 2 |
| H  | Me | Me | Me | 2 |
| Me | H  | H  | Me | 2 |
| Me | H  | H  | Me | 2 |
| Me | H  | Me | H  | 2 |

TABLE 1-continued

[Chemical structure: benzene ring with CH₂NH₂, H₂N, R2, R1, (CH₂)n, O, R3, R4 substituents]

| R1 | R2 | R3 | R4 | n |
|----|----|----|----|---|
| Me | H  | Me | Me | 2 |
| Me | Me | H  | H  | 2 |
| Me | Me | Me | H  | 2 |
| Me | Me | Me | Me | 2 |
| Me | Me | Me | Me | 2 |

(Antioxidant)

Since the diamine derivative of the present invention has antioxidative action, it can prevent the onset and progress of arteriosclerotic lesions by preventing oxidative degeneration of low density lipoproteins (hereinafter, abbreviated as LDL), so it can be applied to treatment agents for arteriosclerosis. Also, it is useful as a treatment agent for various diseases such as senile dementia-related diseases, heart disease, cancer, diabetes, gastrointestinal diseases, burns, eye diseases and kidney disease that are based on oxidative action. Moreover, although various types of active oxygen are generated when blood is reperfused at ischemic sites, and tissue damage is exacerbated due to cell membrane damage caused by lipid peroxidation in ischemic organ diseases such as cerebral stroke and myocardial infarction, the diamine derivative of the present invention is able to prevent tissue damage at sites of ischemic lesions by removing the various types of active oxygen and lipid peroxides due to its antioxidative activity, so it can be applied to treatment agents for ischemic organ disorders. In addition, since the diamine derivative of the present invention has lipoxygenase inhibitory action, it can inhibit the conversion of arachidonic acid to HPETE by inhibiting the action of lipoxygenase.

Moreover, the diamine derivative of the present invention can be used for the prevention and treatment of diseases caused by oxidative disorders of the retina, diabetes, hypertension, arteriosclerosis, anemia, leukemia, connective tissue diseases such as systemic lupus erythematosus or sclerosis, vascular disorders, inflammatory, or degenerative lesions of the retina caused by systemic diseases such as congenital metabolic abnormalities such as Tay-Sacks disease or Vogt-Spielmeyer disease, disorders of retinal blood vessels such as retinopathy of immaturity, retinal vein occlusion, retinal artery occlusion or retinal periphlebitis, inflammation or degeneration of the retina caused by retina detachment or injury, degenerative diseases of the retina accompanying aging such as age-related macular degeneration, or local retina diseases such as congenital retina degenerative diseases, and is particularly useful as a treatment agent for diseases such as age-related macular degeneration that occur due to photooxidative disorders.

(Antioxidant)

The antioxidant according to the present invention is not particularly limited, provided that it contains as its active ingredient at least one selected from the diamine derivatives according to the present invention having the aforementioned antioxidative action and the pharmaceutically acceptable salts thereof, and it can be administered as a drug for the aforementioned diseases by any arbitrary route. Examples of the administration route include oral, transnasal, parenteral, local, transcutaneous or transrectal administration. Its drug form may be a suitable drug form such as a solid, semi-solid, freeze-dried powder or liquid, specific examples of which include tablets, suppositories, pills, soft and hard capsules, powders, liquids, injection preparations, suspensions, aerosols and sustained-release preparations, which allow an accurate dosage to be formulated and administered easily.

In addition, an antioxidant of the present invention can be in the form of a composition that contains in addition to an active ingredient and commonly used pharmaceutical carriers or vehicles, other drugs, adjuvants and so forth within a range that does not react with other ingredients. This composition can be made to contain the active ingredient at 1 to 99% by weight and a suitable pharmaceutical carrier or vehicle at 99 to 1% by weight corresponding to the administration route, and preferably to contain 5 to 75% by weight of the active ingredient and a suitable pharmaceutical carrier or vehicle as the remainder.

In the antioxidant according to the present invention, a small amount of an auxiliary substance such as a lubricant, emulsifier, pH buffer, antioxidant or the like may be contained within a range that does react with the other ingredients as desired regardless of the administration route thereof, examples of which include citric acid, sorbitan monolaurate, triethanol amine oleate and butylated hydroxytoluene.

This type of preparation can be produced according to the conventional method, for example, the description taught in Remington's Pharmaceutical Sciences, Volume 18, Mack Publishing Company, Easton, Pa., 1990.

In the antioxidant of the present invention, the therapeutically effective amount of the compound represented by formula (1) or the pharmaceutically acceptable salt thereof varies according to the individual and the symptoms of the disease being treated. Normally, the daily therapeutically effective dosage may be 0.14 mg to 14.3 mg/day of at least one compound represented by formula (1) or pharmaceutically acceptable salt thereof per 1 kg of body weight, preferably 0.7 mg to 10 mg/day per 1 kg of body weight, and more preferably 1.4 mg to 7.2 mg/day per 1 kg of body weight. For example, in the case of administering to a human having a body weight of 70 kg, the dosage range of the compound of formula (1) or the pharmaceutically acceptable salt thereof is 10 mg to 1.0 g per day, preferably 50 mg to 700 mg per day, and more preferably 100 mg to 500 mg per day. However, this dosage range is meant to serve only as a reference, and the dosage may be made to be outside these ranges according to the symptoms being treated.

Examples of the vehicles contained in the antioxidant for oral administration according to the present invention include any normally used vehicles such as pharmaceutical mannitol, lactose, starch, gelatinized starch, magnesium stearate, sodium saccharine, talc, cellulose ether derivatives, glucose, gelatin, sucrose, citrates and propyl gallate. In addition, the antioxidant for oral administration may also contain a diluent such as lactose, sucrose or dicalcium phosphate, a disintegration agent such as cross carmellose sodium or derivatives thereof, a binder such as magnesium stearate, or a lubricant such as starch, gum arabic, polyvinyl pyrrolidone, gelatin or cellulose ether derivatives.

In the case of using as an injection preparation, sterile, aqueous and non-aqueous solutions, suspensions or emulsions may be contained. Examples of diluents of aqueous solutions and suspensions include distilled water for injection and physiological saline. Examples of diluents of non-aqueous solutions and suspensions include propylene glycol, polyethylene glycol, vegetable oils such as olive oil, alcohols such as ethanol, and Polysorbate (trade name). This type of composition may also additionally contain an additive such as an isotonic agent, antiseptic, lubricant, emulsifier, dispersant, stabilizer (for example, lactose) and solubilization or solubility adjuvant. These can also be used by filtering by passing through a bacteria-retaining filter, producing a solid composition of a disinfectant, and dissolving in sterile water or sterile injection solvent prior to use.

In addition, in the case of using the antioxidant of the present invention in the form of a suppository, a carrier that gradually dissolves in the body such as polyoxyethylene glycol or polyethylene glycol (hereinafter, abbreviated as PEG), specific examples of which include PEG1000 (96%) and PEG4000 (4%), may be used, and an example of such a suppository has 0.5 to 50% by weight of the compound of formula (1) or the pharmaceutically acceptable salt thereof dispersed in the carrier.

In the case of using the antioxidant of the present invention in the form of a liquid, water, saline solution, aqueous dextrose solution, glycerol, ethanol or the like is used as a carrier, and the liquid is preferably in the form of a solution or suspension obtained by treatment such as dissolving or dispersing 0.5 to 50% by weight of the compound of formula (1) or the pharmaceutically acceptable salt thereof along with an arbitrary pharmaceutical adjuvant in the carrier.

(Retina Photooxidative Disorder Inhibitor)

There are no particular limitations on a retina photooxidative disorder inhibitor of the present invention provided that it contains as its active ingredient one or more diamine derivatives of the present invention and pharmaceutically acceptable salts thereof having the aforementioned antioxidative action, and the administration route, administration form and dosage can be the same as the route, form and dosage of the aforementioned antioxidant. In addition, it may also contain the same preparation ingredients, carriers and adjuvants, etc. as the aforementioned antioxidant, one or more types of vehicles, disintegration agents or binders, etc. as well as other retina oxidative disorder inhibitors that do not react with the active ingredient may be suitably added, and ingredients having other pharmacological effects may be suitably contained in addition to the aforementioned ingredients. In addition, the administration form can also be in the form of an ophthalmic solution or ophthalmic ointment in addition to the same administration forms as those of the aforementioned antioxidant.

In the case of using a retina photooxidative disorder inhibitor of the present invention in the form of an ophthalmic solution, it can be obtained in the form of an aqueous solution or suspension by adding the diamine derivative of the present invention to a normally used base solvent, and adjusting the pH to 4 to 10 and preferably to 5 to 9. The ophthalmic solution is preferably subjected to sterilization treatment to obtain a sterile product, and the sterilization treatment can be carried out at any stage of the production process. The concentration of the diamine derivative of the present invention in an ophthalmic solution is 0.001 to 3% (W/V) and preferably 0.01 to 1% (W/V), and the dosage can be several drops each one to four times per day according to the degree of the symptoms, patient status and various other conditions. The aforementioned dosage is meant to serve only as a reference, and the dosage can also be increased beyond these ranges.

Various types of additives such as a buffer, isotonic agent, antiseptic, pH adjuster, thickener, chelating agent or solubilization agent may be suitably added to the aforementioned ophthalmic solution within a range that does not react with a diamine derivative compound of the present invention. Examples of the buffers include citrate buffers, tartrate buffers, acetate buffers and amino acids. Examples of isotonic agents include sugars such as sorbitol, glucose and mannitol, polyvalent alcohols such as glycerin, polyethylene glycol and propylene glycol, and salts such as sodium chloride. Examples of antiseptics include paraoxybenzoic acid esters such as methyl paraoxybenzoate and ethyl paraoxybenzoate, benzyl alcohol, phenethyl alcohol, sorbic acid and salts thereof. Examples of pH adjusters include phosphoric acid and sodium hydroxide. Examples of thickeners include hydroxyethyl cellulose, hydroxypropyl cellulose, methyl cellulose, hydroxypropyl methyl cellulose, carboxymethyl cellulose and salts thereof. Examples of chelating agents include sodium edetate, sodium citrate and condensed sodium phosphate. Examples of solubilization agents include ethanol and polyoxyethylene hardened castor oil.

In addition, in the case of using the retina photooxidative disorder inhibitor of the present invention in the form of an ophthalmic ointment, the diamine derivative of the present invention may be mixed with a normally used ointment base such as purified lanolin, white Vaseline, Macrogol, Plastibase and liquid paraffin, and it is preferably subjected to sterilization treatment to obtain a sterile product. The concentration of the diamine derivative of the present invention in the ophthalmic ointment is normally 0.001 to 3% (W/V) and preferably 0.01 to 1% (W/V), and the number of administrations may be one to four times per day according to the degree of the symptoms, patient status and various other conditions. The aforementioned number of administrations is meant to serve only as a reference, and the number of administrations can also be increased beyond these ranges.

Since a retina photooxidative disorder inhibitor of the present invention has superior antioxidative action, it is effective for the prevention and treatment of degenerative diseases of the retina accompanying aging such as age-related macular degeneration.

Although the following provides a detailed explanation of the diamine derivative of the present invention through its examples, the technical scope of the present invention is not limited to these examples.

EXAMPLE 1

Step 1: Production of 2,2,6,7-tetramethyl-4-nitromethyl-5-nitrodihydrobenzofuran

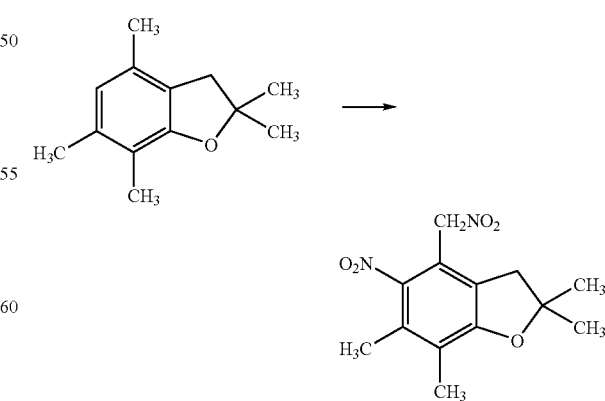

3.80 g of 2,2,4,6,7-pentamethyldihydrofuran were dissolved in 50 ml of acetic anhydride followed by adding in 3.2 ml of nitric acid dropwise while maintaining the temperature at 0° C. After stirring at 0° C. for 2 hours and at room temperature for 2 hours, the solution was poured into an ice-water mixture and stirred for 1 hour at room temperature. After extracting the reaction liquid with ether and washing with saturated saline solution, it was dried with anhydrous magnesium sulfate, the solvent was distilled off under reduced pressure and the residue was purified by silica gel column chromatography (benzene: hexane=1:1, 2,2,4,6,7-pentamethyl-5-nitrodihydrobenzofuran was eluted first followed by the target substance) to obtain 1.40 g of the target substance.

Step 2: Production of 2,2,6,6-tetramethyl-4-aminomethyl-5-aminodihydrobenzofuran-dihydrochloride (Compound No. 1)

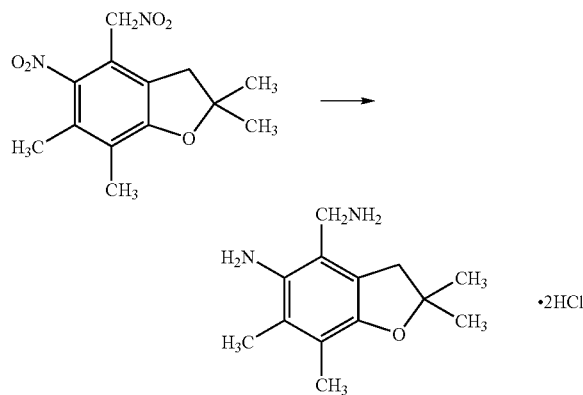

1.40 g of 2,2,6,7-tetramethyl-4-nitromethyl-5-nitrodihydrobenzofuran, 0.35 g of 20% palladium carbon hydroxide and 23 ml of acetic acid were mixed in an autoclave and stirred for 3 hours at room temperature and at a hydrogen pressure of 5 kg/cm². After filtering the reaction liquid with Celite and evaporating the filtrate under reduced pressure, 23.5 ml of methanol and 12 ml of hydrochloric acid were added to the residue followed by refluxing for 30 minutes. After cooling, the reaction liquid was concentrated under reduced pressure and the precipitated crystals were washed with ether to obtain 1.18 g of the target substance. Melting point: 300° C. or higher.

EXAMPLE 2

Production of 2,2,7,8-tetramethyl-5-aminomethyl-6-aminochroman•-dihydrochloride (Compound No. 2)

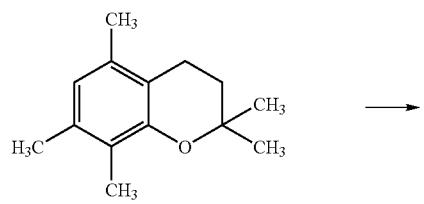

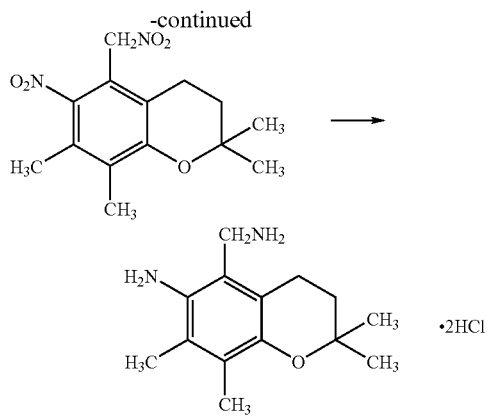

0.70 g of the target substance was obtained in the same manner as Example 1 using 2.0 g of 2, 2, 5, 7, 8-pentamethylchroman instead of 2,2,4,6,7-pentamethyldihydrobenzofuran. Melting point: 219 to 225° C.

Although the structural formulas and physical constants of the compounds produced in the manner described above are shown in Table 2, the present invention is not limited by them. Furthermore, the same abbreviations and symbols are used as those shown in Table 1.

TABLE 2

| Compound No. | R1 | R2 | R3 | R4 | n | Salt | Physical constant |
|---|---|---|---|---|---|---|---|
| 1 | Me | Me | Me | Me | 1 | 2HCl | Melting point: 300° C. or higher |
| 2 | Me | Me | Me | Me | 2 | 2HCl | Melting point: 219 to 225° C. |

EXAMPLE 3

Preparation Production

A preparation containing the compound of the present invention was produced according to the method described below.

Oral Preparation (Tablets Containing 10 mg of Active Ingredient):

| | |
|---|---|
| Compound of present invention | 10 mg |
| Lactose | 81.4 mg |
| Cornstarch | 20 mg |
| Hydroxypropyl cellulose | 4 mg |
| Calcium carboxymethyl cellulose | 4 mg |
| Magnesium stearate | 0.6 mg |
| Total | 120 mg |

50 g of the compound of the present invention, 407 g of lactose and 100 g of cornstarch were uniformly mixed using a fluid bed granulator coating device (manufactured by Okawara MFG. CO., LTD.) to obtain the composition indicated above. 200 g of 10% aqueous hydroxypropyl cellulose solution were then sprayed thereon to produce granules. After drying, the granules were passed through a 20 mesh sieve followed by the addition of 20 g of calcium carboxymethyl cellulose and 3 g of magnesium stearate to obtain tablets containing 120 mg per tablet by using a rotary tablet making machine (manufactured by Hata Iron Works, Ltd.) with a mortar pestle with a dimension of 7 mm×8.4 R.

EXAMPLE 4

Antioxidative Action on Lipids In Vitro

The antioxidative action on lipids in vitro of the compounds according to the present invention was evaluated in accordance with the method of Malvy et al. (Malvy C. et al.,) described in Biochemical and Biophysical Research Communications, 1980, vol. 95, pp. 734 to 737,) by measuring the lipid peroxide activity in a rat brain homogenate. Namely, the rat brain was removed followed by the addition of five volumes of an aqueous solution of phosphate buffered saline (pH 7.4) (hereinafter, abbreviated as PBS) to the brain while cooling with water, homogenizing with a Teflon homogenizer, and centrifuging for 20 minutes at 10,000 g to collect the supernatant as a brain homogenate. 500 μM cysteine, 5 μM ferrous sulfate, and 100 mM KCl were added to the resulting brain homogenate followed by incubating for 30 minutes at 37° C. and measuring the malondialdehyde that formed due to decomposition of lipid peroxide using the thiobarbituric acid method. The 50% inhibitory concentrations (hereinafter, abbreviated as $IC_{50}$) of the compounds according to the present invention were then determined from the measured values. Those results are shown in Table 3. It is apparent that the compounds according to the present invention exhibited antioxidative action for lipids in vitro.

TABLE 3

| Compound No. | 50% inhibitory concentration of anti-lipid peroxide action in vitro ($IC_{50}$, μM) |
| --- | --- |
| 1 | 2.5 |
| 2 | 0.34 |
| Control drug 1 | 1.4 |

A compound described in J. Med. Chem., 40, 559-573 (1997) was used for the control drug. Control drug 1 is the compound shown below.

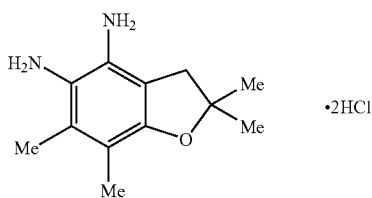

EXAMPLE 5

Tissue Migration

Tissue migration of the compounds according to the present invention was evaluated by measuring the antioxidative action on lipids ex vivo. A test compound dissolved or suspended in an aqueous physiological saline solution or aqueous physiological saline solution containing 1% polyethylene hardened castor oil (Nikko Chemicals: Nikkol HCO-60) was intraperitoneally administered to male SD rats (age: 6 weeks) (purchased from Japan SLC) in groups of 3 animals each at a dose of 100 mg/kg. The animals were sacrificed by exsanguination by severing the carotid artery 30 minutes after administration followed by removing the brain, heart and kidneys. The lipid peroxide activity of homogenates of each tissue was measured using the method described in Example 4. The inhibition rates of the test compounds in each tissue were determined from the amounts of lipid peroxide formed in a control group (physiological saline dose group) and test compound groups. Those results are shown in Table 4. On the basis of these results, the compounds of the present invention clearly had a high degree of tissue migration.

TABLE 4

| | Inhibition rate of ex vivo anti-lipid peroxide action (%) | | |
| --- | --- | --- | --- |
| Compound No. | Brain | Heart | Kidney |
| 1 | 93 | 81 | 83 |
| 2 | 98 | 96 | 97 |
| Control Drug 1 | 94 | 84 | 87 |

EXAMPLE 6

Antioxidative Action In Vivo

The antioxidative action in vivo of the compounds according to the present invention was evaluated according to the method described in the Journal of Medical Chemistry (J. Med. Chem., 1997, vol. 40, pp. 559 to 573) based on the inhibitory effects on abnormal behavior and mortality rate following administration of ferrous chloride into the spinal subarachnoid cavity of mice. Male Slc:ICR mice (age: 5 weeks) (purchased from Japan SLC) were used in groups of 3 to 7 animals each, and were administered 5 μl of aqueous physiological saline solution containing 50 mM ferrous chloride into the spinal column between the 5th and 6th lumbar vertebra. Symptoms were observed for 20 to 60 minutes following administration of ferrous chloride, and scores were determined after 60 minutes based on the symptoms shown in Table 5. The test compounds were dissolved or suspended in an aqueous physiological saline solution or an aqueous physiological saline solution containing 1% polyethylene hardened castor oil (manufactured by Nikko Chemicals CO., LTD. under the name of NIKKOL HCO-60), and administered intraperitoneally or orally 30 minutes before the administration of ferrous chloride. The 50% inhibitory dose (hereinafter, abbreviated as $ID_{50}$) of each test compound was determined from the score of a control group (physiological saline treated group) and the score of each test compound treated group. Those results are shown in Table 6. It is apparent on the basis of these results that the compounds according to the present invention had the antioxidative action in vivo.

TABLE 5

| Score | Symptoms |
| --- | --- |
| 0 | Normal |
| 1 | Frequent biting of lower abdomen or end of posterior trunk |
| 2 | Observation of at least one of the following changes: (1) Frequent biting of posterior trunk while turning around (2) Hypersensitivity and attacking response to external stimuli (3) Trembling |
| 3 | Clonic convulsion |
| 4 | Tonic convulsion or paralysis of posterior trunk |
| 5 | Death |

TABLE 6

| Compound No. | Antioxidative action in vivo 50% inhibitory dose ($ID_{50}$ mg/kg) | |
|---|---|---|
| | Intraperitoneal administration | Oral administration |
| 1 | 1.8 | 6 |
| 2 | 2.6 | 12 |
| Control Drug 1 | >30 | >30 |

EXAMPLE 7

Retina Migration

The retina migration of the compounds according to the present invention was evaluated. The test compounds dissolved or suspended in 0.1 N aqueous hydrochloric acid solution or 1% polyethylene hardened castor oil (Nikkol HCO-60) solution were orally administered to male SD rats (age: 6 weeks) in groups of three animals each followed by removing both eyes 30 minutes later and separating the retinas while cooling with ice. The retinas were homogenized with a Polytron Microhomogenizer (NS-310E: manufactured by Niti-On Medical and Physical Instruments) in 0.1 M Tris-HCl buffer (pH 7.4) while cooling with ice to prepare 5% homogenates. The homogenates were then auto-oxidized for 1 hour at 37° C., and the amounts of lipid peroxide that formed were quantified using the thiobarbituric acid method (Masugi, et al., Vitamin, 51, 21 to 29, 1977). The dose that resulted in 30% inhibition ($ID_{30}$) was determined from the inhibition rate at each dose level. Those results are shown in Table 7. It is apparent on the basis of these results that the compounds according to the present invention had action that inhibits the formation of lipid peroxides in the retina ex vivo, and exhibited a high degree of retina migration.

TABLE 7

| Compound No. | Inhibitory effect on formation of lipid peroxides in retina ex vivo 30% inhibitory concentration ($ID_{30}$ mg/kg, oral administration) |
|---|---|
| 1 | 16 |
| 2 | 6.9 |

EXAMPLE 8

Inhibitory Action on Increases in 66 kDa Protein

The inhibitory action of the compound according to the present invention on increases in 66 kDa protein in rat retina irradiated with UV light was evaluated. The test compound was dissolved or suspended in 0.1 N aqueous hydrochloric acid solution or 1% polyethylene hardened castor oil (Nikkol HCO-60) and orally administered to male Wistar rats (age: 7-9 weeks) followed 30 minutes later by irradiation of the right eye with UV-A (12 mW/cm$^2$) for 30 minutes using a UV spot light source. In addition, the left eye was not irradiated and used as a control. The rats were housed in an environment blocked from interior light both during UV-A irradiation and for 2 hours before and after irradiation. The retinas were separated 48 hours after irradiation and 5% homogenates were prepared using the same method as described in Example 4. Changes in retina protein were determined by SDS-polyacrylamide gel electrophoresis in accordance with the method of Lammli (Nature, 277, 680 to 685, 1970). Namely, the retina homogenates were electrophoresed using 4.5% gel (pH 6.8) for concentration and 10% gel (pH 8.8) for separation in 20 mM electrophoresis buffer (25 mM Tris, 192 mM glycine, 0.1% SDS) at a constant current (limit: 300 V). Following electrophoresis, the gel was fixed with 15% TCA and then a mixture of ethanol, acetic acid, and water (25:8:65) followed by staining with a mixture of ethanol, acetic acid, and water (9:2:9) containing 0.25% Coumassie Brilliant Blue R-250. Subsequently, the gel was decolored with a mixture of ethanol, acetic acid, and water (25:8:65) and the 66 kDa protein following electrophoresis was analyzed by densitrography. The amount of protein in the samples was determined using the Lowry method. Those results are shown in Table 8. It is apparent on the basis of these results that the compound according to the present invention significantly inhibited increases in 66 kDa protein.

TABLE 8

| Compound No. (N = 3) | Ratio of 66 kDa protein in UV-irradiated rat retina (right eye: irradiated/left eye: non-irradiated) |
|---|---|
| Normal group | 1 |
| Control group | 4.48 |
| 1 (100 mg/kg, p.o.) | 1.45 |

EXAMPLE 9

Inhibitory Action on 5-Lipoxygenase (5-LO) and 15-Lipoxygenase (15-LO)

5-LO inhibitory activity was measured using a variation of the method of Carter et al. (Carter G. W. et al., J. Pharmacol. Exp. Ther., 256, 929 to 937, 1991). Namely, after pre-incubating (37° C., 15 minutes) in Hank's solution human peripheral blood mononuclear cells and a test compound dissolved in DMSO (final concentration: 1%), 30 µM A23187 was added and the resulting solution was additionally incubated (37° C., 30 minutes). The resulting leucotriene B4 that formed was quantified by enzyme immunoassay, and the 50% formation inhibitory concentration (µM) of the test compound with respect to 5-LO was calculated from that value. Those results are shown in Table 9.

15-LO inhibitory activity was measured using a variation of the method of Auerbach et al. (Auerbach B. J. et al., Anal. Biochem., 201, 375 to 380, 1992). Namely, after pre-incubating (4° C., 15 minutes) in phosphate buffer (pH 7.4) 15-LO obtained from rabbit reticulocytes and a test compound dissolved in DMSO (final concentration: 1%), 256 µM linoleic acid was added and the resulting solution was additionally incubated (4° C., 10 minutes). The resulting 15-HETE that formed was quantified by spectrophotometry ($OD_{660}$ nm), and the 50% formation inhibitory concentration (µM) of the test compound with respect to 15-LO was calculated from that value. Those results are shown in Table 9. It is apparent on the basis of these results that the compound of the present invention had inhibitory action on 5-lipoxygenase (5-LO) and 15-lipoxygenase (15-LO).

TABLE 9

| | Lipoxygenase inhibitory action 50% inhibitory concentration (IC$_{50}$ μm) | |
|---|---|---|
| Compound No. | 5-LO | 15-LO |
| 1 | >10 (31%) | 3.74 |
| Control Drug 2 | >10 (34%) | 3.26 |

EXAMPLE 10

Acute Oral Toxicity

A single dose of the test compounds according to the present invention was orally administered to male mice followed by observing for 7 days to determine the mortality rate. Those results are shown in Table 10. The compound indicated below was used for Control Drug 3.

It is apparent on the basis of these results that the compound according to the present invention had a low degree of acute oral toxicity.

TABLE 10

| Compound No. | Mouse acute oral toxicity (LD$_{50}$ mg/kg) |
|---|---|
| 1 | >1000 |
| 2 | >1000 |
| Control Drug 2 | <300 |

INDUSTRIAL APPLICABILITY

The diamine derivative of the present invention or the pharmaceutical acceptable salt thereof has antioxidative activity that is effective for the treatment of arteriosclerosis as well as ischemic organ disorders such as myocardial infarction and cerebral stroke, or for the treatment of diseases caused by oxidative cytotoxicity, is able to effectively inhibit retina disorders caused by photooxidation or the like, can be used in the form of a superior antioxidant that contains the diamine derivative compound according to the present invention, and is useful as a drug for inhibiting oxidative disorders of the retina that demonstrates few adverse side effects.

The invention claimed is:

1. A compound represented by formula (1):

(1)

(wherein R1, R2, R3 and R4 respectively and independently represent a hydrogen atom or a C$_{1-6}$ alkyl group, and n represents an integer of 1 or 2).

2. A production process of a compound represented by formula (1):

(1)

(wherein, R1, R2, R3 and R4 respectively and independently represent a hydrogen atom or a C$_{1-6}$ alkyl group, and n represents an integer of 1 or 2) comprising:
  a step 1 in which a compound represented by formula (3):

(3)

(wherein, R1, R2, R3, R4 and n are the same as previously defined) is obtained by nitrating a compound represented by formula (2):

(2)

(wherein, R1, R2, R3, R4 and n are the same as previously defined); and,
  a step 2 in which hydrogenation is carried out using a reducing agent on the compound represented by formula (3).

3. An antioxidant comprising as its active ingredient at least one compound represented by formula (1):

(1)

(wherein, R1, R2, R3 and R4 respectively and independently represent a hydrogen atom or a C$_{1-6}$ alkyl group, and n represents an integer of 1 or 2) or pharmaceutically acceptable salt thereof.

* * * * *

UNITED STATES PATENT AND TRADEMARK OFFICE
CERTIFICATE OF CORRECTION

PATENT NO. : 7,652,155 B2
APPLICATION NO. : 10/552015
DATED : January 26, 2010
INVENTOR(S) : Nobuhiro Umeda et al.

It is certified that error appears in the above-identified patent and that said Letters Patent is hereby corrected as shown below:

Title Page, Item (75) Inventors: Lines 2-4
"Seiichi Uchida, Odawara (JP)" should be --Seiichi Uchida, Naka-gun (JP)--;
"Seiichi Ikeyama, Odawara (JP)" should be --Seiichi Ikeyama, Yokohama-shi (JP)--.

Title Page, (*) Notice: delete "533 days" and insert --1005 days--.

Signed and Sealed this

Fourteenth Day of September, 2010

David J. Kappos
*Director of the United States Patent and Trademark Office*